United States Patent [19]

Hirsch

[11] 4,075,351
[45] Feb. 21, 1978

[54] INHIBITION OF MALE FERTILITY WITH ALIPHATIC SULFAMATES

[75] Inventor: Allen Frederick Hirsch, Somerville, N.J.

[73] Assignee: Ortho Pharmaceutical Corporation, Raritan, N.J.

[21] Appl. No.: 711,188

[22] Filed: Aug. 3, 1976

Related U.S. Application Data

[62] Division of Ser. No. 537,613, Dec. 30, 1974, Pat. No. 3,997,585.

[51] Int. Cl.² ............... A61K 31/255; A61K 31/18; A61K 31/455

[52] U.S. Cl. .................... 424/303; 424/267; 424/321

[58] Field of Search ............ 424/321, 303, 267

[56] References Cited

U.S. PATENT DOCUMENTS 3,927,090  12/1975  Goralski et al. .............. 424/321

Primary Examiner—Frederick E. Waddell
Attorney, Agent, or Firm—Benjamin F. Lambert

[57] ABSTRACT

Aliphatic sulfamates are prepared by reacting an alkanediol with sulfamoyl chloride. The aliphatic sulfamates are novel compounds and are useful in the control of fertility in male animals.

5 Claims, No Drawings

INHIBITION OF MALE FERTILITY WITH ALIPHATIC SULFAMATES

This is a division of application Ser. No. 537,613, filed Dec. 30, 1974 now U.S. Pat. No. 3,997,585.

BACKGROUND OF THE INVENTION

The present invention relates to novel aliphatic sulfamates. The sulfamates may be represented by the formula:

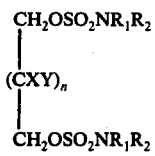

wherein $n$ is an integer from 0–8 and X and Y are hydrogen, provided that when $n$ is 1, X and Y are hydrogen, lower alkyl having 1-3 carbon atoms, aryl such as phenyl or arylalkyl such as benzyl, phenethyl and the like, and $R_1$ and $R_2$ are hydrogen, alkyl having 1-7 carbon atoms, aryl, arylalkyl such as benzyl, phenethyl, phenylpropyl and the like, cycloalkyl such as cyclopentyl, cyclohexyl and the like, or $R_1$ and $R_2$ together with the nitrogen atom to which they are attached form a saturated heterocyclic ring. Preferred among these compounds are those compounds wherein $R_1$ and $R_2$ are hydrogen.

The novel aliphatic sulfamates of the present invention are prepared by reacting an alkanediol with a sulfamoyl halide in a suitable solvent in the presence of a strong base. Suitable alkanediols which may be employed include 1,2-ethanediol, 1,3-propanediol, 1,4-butanediol, 1,5-pentanediol, 1,10-decanediol and the like. As the halide reactant, sulfamoyl chloride and N,N-di or mono substituted sulfamoyl halides may be employed. Bases such as sodium hydride, sodium amide, sodium hydroxide, pyridine and tributyltin are examples of suitable strong bases. Examples of solvents which may be employed include 1,2-dimethoxyethane, ether, tetrahydrofuran, diglyme and p-dioxane. The reaction with the sulfamoyl halide may be carried out at room temperature, but it is preferred to carry out the reaction at a temperature between 0°–10° C. The sulfamate is obtained from the reaction mixture by techniques known to those skilled in the art.

The novel aliphatic sulfamates are useful in the control of fertility in male animals. The compounds are capable of interfering with sperm as they sojourn in the epididymis and thus result in what is known as functional sterility, i.e. the gametes remain morphologically normal and show motility but normal fertilization is not achieved. Generally dosage levels of from about 5-200 mg./kg. are effective in inducing functional sterility. The preferred dosage range is from about 10-150 mg./kg. In addition to causing functional sterility of epididymal sperm, the novel sulfamates have antiandrogenic properties as manifested by inhibition of the size of the ventral prostate.

The general procedure followed to determine the activity of compounds which inhibit male fertility by altering the functional capacity of epididymal sperm is as follows:

A two week dosing period (i.e., the approximate period required for sperm transport through the epididymis) enables separation of those drugs which affect epididymal sperm maturation and/or function from the antispermatogenic agents which have a longer delay in the onset of sterility. Each individual test involves 5 male rats (250-300 g.) caged togehter in air conditioned animal quarters and maintained on laboratory chow and tap water ad libitum. The compound to be tested is dissolved or suspended in appropriate vehicles (usually methylcellulose) and administered daily (usually i.g.) for 14 consecutive days. Control animals receive the vehicle only. At the end of the 14th day of treatment each male is individually caged with a proestrus female. Vaginal smears are checked the following morning for evidence of positive mating, and those males failing to mate are recohabited with proestrus females the following night. Males are sacrificed and autopsied the day after cohabitation for a gross examination of testes, epididymides, and accessory sex organs. Tissue samples of these organs are preserved for histological processing if observation yields a possible effect. Females (regardless of sperm presence in the vaginal washings) are autopsied 14 days after cohabitation to examine for pregnancy.

The inability of females to produce a viable embryo following a successful mating with treated males (two weeks of medication) is used as a measure of functional infertility. The number of males mating of those cohabited gives a gross indication of the drug's effect on libido. The size of the accessory sex organs provides an indication of the effect on androgen production. Microscopic analysis of epididymal sperm provides information on sperm quality (motility and morphology) and quantity.

The following examples describe the invention in greater particularity and are intended to be a way of illustrating and not limiting the invention.

EXAMPLE 1

1,2-Bis-O-sulfamyl-1,2-ethanediol

A 57% oil dispersion of sodium hydride (8.45 g.; 0.20 mol.) is added to a solution of ethylene glycol (3.1 g.; 0.05 mol.) in 1,2-dimethoxyethane (100 ml.). The resulting suspension is stirred at room temperature for 2 hours and then cooled to +4° C. Sulfamoyl chloride (20.79 g.; 0.18 mol.) is dissolved in 1,2-dimethoxyethane (400 ml.) and added dropwise to the solution with stirring. The reaction mixture is stirred at +4° C for an additional 24 hours. A precipitate forms which is filtered off and the filtrate is concentrated. The residue is partitioned between heptane and methanol, and the methanol solution is concentrated to a syrup which crystallizes from ethyl acetate to yield 6.1 g. (58%) of 1,2-bis-O-sulfamyl-1,2-ethanediol, m.p. 96.5°–99° C. When in the above procedure 1,5-pentanediol is employed in place of ethylene glycol, 1,5-bis-O-sulfamyl-1,5-pentanediol is obtained.

EXAMPLE 2

1,10-Bis-O-sulfamyl-1,10-decanediol

A 57% oil dispersion of sodium hydride (8.45 g.; 0.20 mol.) is added to a solution of 1,10-decanediol (8.71 g.; 0.05 mol.) in 1,2-dimethoxyethane (100 ml.). The resulting solution is stirred at room temperature for 2 hours and then cooled to +4° C. Sulfamoyl chloride (20.79 g.; 0.18 mol.) is dissolved in 1,2-dimethoxyethane (400 ml.) and added dropwise to the solution with stirring. The reaction mixture is stirred at +4° C for an additional 48 hours. A precipitate forms which is filtered off and the filtrate is concentrated. The residue is partitioned between heptane and methanol and the methanol solution is concentrated to a syrup which crystallizes from ethyl acetate to yield 6.0 g. (36%) of 1,10-bis-O-sulfamyl-1,10-decanediol, m.p. 129°–131° C.

When in the above procedure 1,6-hexanediol is employed in place of 1,10-decanediol, 1,6-bis-O-sulfamyl-1,6-hexanediol is obtained.

EXAMPLE 3

1,4-Bis-O-sulfamyl-1,4-butanediol

A 57% oil dispersion of sodium hydride (8.45 g.; 0.20 mol.) is added to a solution of 1,4-butanediol (4.5 g.; 0.05 mol.) in 1,2-dimethoxyethane (100 ml.). The resulting solution is stirred at room temperature for 2 hours and then cooled to +4° C. Sulfamoyl chloride (20.79 g.; 0.18 mol.) is dissolved in 1,2-dimethoxyethane (400 ml.) and added dropwise to the solution with stirring. The reaction mixture is stirred at +4° C for an additional 48 hours. A precipitate forms which is filtered off and the filtrate is concentrated. The residue is partitioned between heptane and methanol and the methanol solution is concentrated to a syrup which crystallizes from ethyl alcohol to yield 5.5 g. (47%) of 1,4-bis-O-sulfamyl-1,4-butanediol, m.p. 126°–129° C.

When in the above procedure 1,7-heptanediol is employed in place of 1,4-butanediol, 1,7-bis-O-sulfamyl-1,7-heptanediol is obtained.

EXAMPLE 4

1,3-Bis-O-sulfamyl-1,3-propanediol

A 57% oil dispersion of sodium hydride (25.4 g.; 0.60 mol.) is added to a solution of 1,3-propanediol (11.41 g.; 0.15 mol.) in 1,2-dimethoxyethane (100 ml.). The resulting solution is stirred at room temperature for 2 hours and then cooled to +4° C. Sulfamoyl chloride (62.37 g.; 0.54 mol.) is dissolved in 1,2-dimethoxyethane (400 ml.) and added dropwise to the solution with stirring. The reaction mixture is stirred at +4° C for an additional 24 hours. A precipitate forms which is filtered off and the filtrate is concentrated. The residue is partitioned between heptane and methanol and the methanol solution is concentrated to a syrup. The residue is washed with heptane and chromatographed through SilicAR, CC-7 using 50% acetone-chloroform as the eluent. The fractions are collected and upon removal of the solvent 1,3-bis-O-sulfamyl-1,3-propanediol is obtained as a crystalline residue, m.p. 85°–87.5° C.

When in the above procedure 1,8-octanediol and 1,9-nonanediol are employed in place of 1,3-propanediol, 1,8-bis-O-sulfamyl-1,8-octanediol and 1,9-bis-O-sulfamyl 1,9-nonanediol respectively are obtained.

EXAMPLE 5

2-Methyl-2-propyl-1,3-bis-O-sulfamyl-1,3-propanediol

To a solution of 10 g. (0.076 mol.) of 2-methyl-2-propyl-1,3-propanediol in 200 ml. of dimethoxyethane is added 12.7 g. (0.3 mol.) of 57% sodium hydride followed by an additional 400 ml. of dimethoxyethane. After stirring overnight the suspension is cooled to 4° C and a solution of 31.2 g. (0.27 mol.) of sulfamoyl chloride in 600 ml. of dimethoxyethane is added dropwise. The resulting suspension is stirred overnight at room temperature. The mixture is then filtered, the filtrate is concentrated and the residue washed with heptane. The residue is then chromatographed through SilicAR, CC-7 and eluted with 25% acetone-chloroform. The solid obtained after removal of the solvent is crystallized from a mixture of ethyl acetate-hexane-methylene chloride to afford 2-methyl-2-propyl-1,3-bis-O-sulfamyl-1,3-propanediol, m.p. 92°–94° C.

When in the above procedure 2-ethyl-2-propyl-1,3-propanediol, 2,2-dimethyl-1,3-propanediol and 2-methyl-1,3-propanediol are employed instead of 2-methyl-2-propyl-1,3-propanediol, 2-ethyl-2-propyl-1,3-bis-O-sulfamyl-1,3-propanediol, 2,2-dimethyl-1,3-bis-O-sulfamyl-1,3-propanediol and 2-methyl-1,3-bis-O-sulfamyl-1,3-propanediol, respectively, are obtained.

EXAMPLE 6

2,2-Diphenyl-1,3-bis-O-sulfamyl-1,3-propanediol

To a solution of 17.3 g. (0.076 mol.) of 2,2-diphenyl-1,3-propanediol in 200 ml. of dimethoxyethane is added 12.7 g. (0.3 mol.) of 57% sodium hydride followed by an additional 400 ml. of dimethoxyethane. After stirring overnight the suspension is cooled to 4° C. A solution of 31.2 g. (0.27 mol.) of sulfamoyl chloride in 600 ml. of dimethoxyethane is then added dropwise. The suspension is stirred overnight at room temperature. After filtering the mixture the filtrate is concentrated and the residue washed with heptane. Chromatography on SilicAR, CC-7, followed by crystallization affords 2,2-diphenyl-1,3-bis-O-sulfamyl-1,3-propanediol.

When in the above procedure 2,2-dibenzyl-1,3-propanediol and 2,2-dicyclohexyl-1,3-propanediol are employed in place of 2,2-diphenyl-1,3-propanediol, 2,2-dibenzyl-1,3-bis-O-sulfamyl-1,3-propanediol and 2,2-dicyclohexyl-1,3-bis-O-sulfamyl-1,3-propanediol are obtained.

EXAMPLE 7

1,2-Bis-O-(N,N-dimethylsulfamyl)-1,2-ethanediol

A 57% oil dispersion of sodium hydride (8.45 g.; 0.20 mol.) is added to a solution of ethylene glycol (3.1 g.; 0.05 mol.) in 1,2-dimethoxyethane (100 ml.). The resulting suspension is stirred at room temperature for 2 hours and then cooled to +4° C. N,N-dimethylsulfamoyl chloride, 25.8 g. (0.18 mol.), is dissolved in 1,2-dimethoxyethane (400 ml.) and added dropwise to the solution with stirring. The reaction mixture is stirred at +4° C for an additional 24 hours. A precipitate forms which is filtered off and the filtrate is concentrated. The residue is partitioned between heptane and methanol, and the methanol solution is concentrated to a syrup which crystallizes from ethyl acetate to yield 1,2-bis-O-(N,N-dimethylsulfamyl)-1,2-ethanediol.

When in the above procedure N,N-diphenylsulfamoyl chloride and N-ethylsulfamoyl chloride are employed in place of sulfamoyl chloride, 1,2-bis-O-(N,N-diphenylsulfamyl)-1,2-ethanediol and 1,2-bis-O-(N-ethylsulfamyl)-1,2-ethanediol are obtained.

When in the above procedure N-cyclohexylsulfamoyl chloride, N,N-dicyclopentylsulfamoyl chloride, N,N-dibenzylsulfamoyl chloride and 1-piperidylsulfonyl chloride are employed in place of sulfamoyl chloride, 1,2-bis-O-(N-cyclohexysulfamyl)-1,2-ethanediol, 1,2-bis-O-(N,N-dicyclopentylsulfamyl)-1,2-ethanediol, 1,2-bis-O-(N,N-dibenzylsulfamyl)-1,2-ethanediol and 1,2-bis-(1-piperidylsulfonyl)-1,2-ethanediol are obtained.

What is claimed is:

1. A method of inhibiting fertility in male animals comprising administering to a male animal an effective amount of a compound of the formula

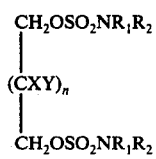

wherein $n$ is an integer from 0 to 8 and X and Y are hydrogen, provided that when $n$ is 1, X and Y are hydrogen, lower alkyl having 1–3 carbon atoms, phenyl, benzyl or phenethyl, $R_1$ and $R_2$ are hydrogen, alkyl having 1–7 carbon atoms, phenyl, benzyl, phenethyl or cycloalkyl having 5–6 carbon atoms, and $R_1$ and $R_2$ together with the nitrogen are piperidyl.

2. The method of claim 1 wherein said compound is 1,2-bis-O-sulfamyl-1,2-ethanediol.

3. The method of claim 1 wherein said compound is 1,3-bis-O-sulfamyl-1,3-propanediol.

4. The method of claim 1 wherein said compound is 1,4-bis-O-sulfamyl-1,4-butanediol.

5. The method of claim 1 wherein said compound is 1,10-bis-O-sulfamyl-1,10-decanediol.

* * * * *